US011185504B2

(12) United States Patent
Sallam et al.

(10) Patent No.: US 11,185,504 B2
(45) Date of Patent: Nov. 30, 2021

(54) TRANSDERMAL NON-AQUEOUS NANOEMULGELS FOR SYSTEMIC DELIVERY OF AROMATASE INHIBITOR

(71) Applicant: QATAR UNIVERSITY

(72) Inventors: Assayed AlArabi Nauman Sallam, Amman (JO); Husam M. Younes, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 16/957,017

(22) PCT Filed: Dec. 19, 2018

(86) PCT No.: PCT/IB2018/060292

§ 371 (c)(1),
(2) Date: Jun. 22, 2020

(87) PCT Pub. No.: WO2019/123282

PCT Pub. Date: Jun. 27, 2019

(65) Prior Publication Data

US 2020/0390701 A1 Dec. 17, 2020

Related U.S. Application Data

(60) Provisional application No. 62/610,095, filed on Dec. 22, 2017.

(51) Int. Cl.

| | |
|---|---|
| ***A61K 9/107*** | (2006.01) |
| ***A61K 9/06*** | (2006.01) |
| ***A61K 31/4196*** | (2006.01) |
| ***A61K 47/14*** | (2017.01) |
| *A61K 9/00* | (2006.01) |
| *B82Y 5/00* | (2011.01) |

(52) U.S. Cl.
CPC .............. *A61K 9/1075* (2013.01); *A61K 9/06* (2013.01); *A61K 31/4196* (2013.01); *A61K 47/14* (2013.01); *A61K 9/0014* (2013.01); *B82Y 5/00* (2013.01)

(58) Field of Classification Search
CPC ...... A61K 9/06; A61K 31/4196; A61K 47/14; A61K 9/0014; B82Y 5/00
See application file for complete search history.

(56) References Cited

U.S. PATENT DOCUMENTS

| | | | |
|---|---|---|---|
| 2009/0246159 | A1 | 10/2009 | Bui et al. |
| 2012/0093896 | A1 | 4/2012 | Mangiat et al. |
| 2014/0242016 | A1 | 8/2014 | Binks et al. |
| 2017/0266289 | A1 | 9/2017 | Lipari et al. |
| 2017/0312190 | A1 | 11/2017 | Gonazales et al. |

OTHER PUBLICATIONS

International Search Report and Written Report issued in PCT/IB18/60292 dated May 2, 2019.

*Primary Examiner* — Robert S Cabral
(74) *Attorney, Agent, or Firm* — Squire Patton Boggs (US) LLP

(57) ABSTRACT

Transdermal nanoemugels for systemic delivery of potent drugs like aromatase inhibitors letrozole and anastrozole are disclosed. The disclosed compositions may include gelling agent, surfactants, cosolvents, and oily components. The process of preparing the nanoemulgels is simple and the formation of nanoemulgels is spontaneous. Penetration enhancers are included in the compositions of the transdermal nanoemugels. The compositions have penetration power with emollient effects to the skin. The transdermal drug delivery system may be applied to skin in a single dose that produces pharmacologically effective blood concentration of the potent drug for one week or up to one month depending on the amount and thickness of the applied nanoemugels in the transdermal matrix patches.
The nanoemulgels can be used for topical delivery of NSAID.

32 Claims, 1 Drawing Sheet

Effect of Type of Penetration Enhancers on
Diffusion of LZ from NEGMS using Start™ Membrane for 15 days

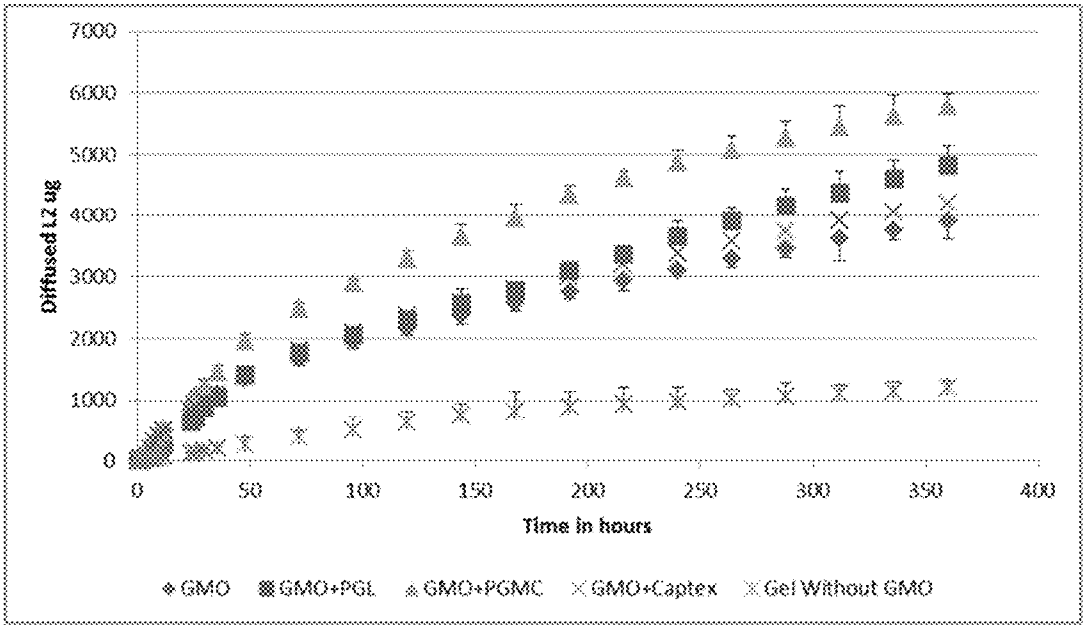

LZ = letrozole
NEGMS = Nano Emul Gel Matrix System
GMO = Glyceryl monooleate grade above 40% glycerylmonooleate content.
PGL = Propylene Glycol Laurate'
PGMC = Propylene Glycol Mono Caprylate
Captex = Captex 170 EP (Caprylic/Capric Acid Ester of Saturated Fatty Alcohol C12-C18).

TRANSDERMAL NON-AQUEOUS NANOEMULGELS FOR SYSTEMIC DELIVERY OF AROMATASE INHIBITOR

This U.S. National Stage patent application claims priority to PCT Patent Application serial number PCT/IB2018/060292, filed on Dec. 19, 2018, from which the PCT Patent Application claims priority to U.S. Provisional Patent Application Ser. No. 62/610,095, filed on Dec. 22, 2017. The entire contents of each of the aforementioned patent applications are expressly incorporated herein by reference in their entirety.

FIELD OF INVENTION

The present invention relates to transdermal drug delivery systems (TDDS) of potent drugs for a short or long period, particularly pharmaceutical compositions for transdermal delivery of potent drugs and a method of making the compositions. The compositions are nanoemulgels. The drugs are aromatase inhibitor such as letrozole or anti-inflammatory and analgesic drugs such as NSAIDs.

BACKGROUND

Worldwide, breast cancer is the leading type of cancer in women, accounting for 25% of all cases according to a *World Cancer Report* 2014 by World Health Organization. In 2012, it resulted in 1.68 million new cases and 522,000 deaths according to the same report. There is a need for effective treatment of breast cancer.

Some breast cancers require estrogen to continue growing. Aromatase is the enzyme that synthesizes estrogen. Aromatase inhibitors work by inhibiting the action of the enzyme aromatase. Because these breast cancers respond to estrogen, lowering or blocking estrogen production at the site of the cancer (i.e. the adipose tissue of the breast) with aromatase inhibitors has been proven an effective treatment for hormone-sensitive breast cancer in postmenopausal women. Aromatase inhibitors (AIs) are a class of drugs used in the treatment of breast cancer in postmenopausal women and gynecomastia in men. Letrozole is a non-steroidal aromatase inhibitor for the treatment of hormonally-responsive breast cancer after surgery. It is currently marketed as oral formulation.

The present inventors have developed non-aqueous nanoemulgels for topical or transdermal delivery of potent drugs, particularly aromatase inhibitors such as letrozole and anastrozole. The non-aqueous nanoemulgels may also be used for topical or transdermal delivery of analgesic drugs such as nonsteroidal anti-inflammatory drugs (NSAIDs). Exemplary NSAIDs are diclofenac diethylamine and ibuprofen.

While transdermal drug delivery is often developed as a patch, it can be developed using a gel which is utilized as a topical application or as a drug reservoir in transdermal patch delivery system. Drug contained in the gel then permeates the skin and enters the bloodstream. Transdermal drug delivery systems (TDDs) have advantages over conventional oral formulation such as controllably releasing a drug over a short time period or a long-time period, and directly delivering a drug into blood circulation thus avoiding drug degradation in gastrointestinal tract and hepatic first-pass effect. TDDS shall produce more steady blood concentration which avoids peaks and troughs in drug plasma levels. This shall result in less side effects. Furthermore, TDDS has better patient compliance.

SUMMARY OF THE INVENTION

In one embodiment of the present invention, it is provided a non-aqueous nanoemulgel comprising a therapeutic agent, a hydrophilic continuous phase formed of cosolvents, an oily dispersed phase formed of an oil component, and an emulsifying gelling agent. The oil component comprises glyceryl monooleate (GMO) and isohexadecane. The grade of GMO is more than 40% glyceryl monooleate content. In some embodiments, the oily dispersed phase forms nanoglobules. In some embodiments, the cosolvents form nanoglobules of the oily dispersed phase. The size of the nanoglobules is less than 500 nm in diameter. The nanoemulgel is a clear gel. In some embodiments, the nanoemulgel further comprises a penetration enhancer. In some embodiments, the emulsifying gelling agent is SEPINEO P 600.

In one embodiment of the present invention, it is provided a method of making a non-aqueous nanoemulgel disclosed above, the method comprising:

mixing an oil component and an emulsifying gelling agent to form a first mixture; wherein the oil component comprises glyceryl monooleate (GMO) and isohexadecane; the grade of GMO is that having more than 40% glyceryl monooleate content; and preferably the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel. Each mixture is mixed well using appropriate mixing techniques known in the art. As an alternative, the therapeutic agent can be dissolved in the first cosolvent mixed with a portion of the second cosolvent to form a second mixture. In such case, the remaining portion of the second cosolvent is added to the third mixture thereby forming a naoemulgel.

In some embodiments, the method further comprises adding a penetration enhancer to the first mixture, the second mixture, the third mixture, or the final mixture.

In one embodiment of the present invention, it is provided a method of making a non-aqueous nanoemulgel, the method comprising:

mixing an oil component, and an emulsifying gelling agent to form a first mixture; wherein the oil component comprises glyceryl monooleate (GMO) and isohexadecane; the grade of GMO is that having more than 40% glyceryl monooleate content; preferably the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel. Each mixture is mixed well using appropriate mixing techniques known in the art. As an alternative, the therapeutic agent can be dissolved in the first cosolvent mixed with a portion of the second cosolvent to form a second mixture. In such case, the remaining portion of the second cosolvent is added to the third mixture thereby forming a naoemulgel. The nanoemulgel is a clear gel.

In some embodiments, the oily dispersed phase forms nanoglobules. In some embodiments, the cosolvents form nanoglobules of the oily dispersed phase. The size of the nanoglobules is less than 500 nm in diameter.

In some embodiments, the method further comprises adding a penetration enhancer to the first mixture, the second mixture, the third mixture, or the final mixture.

In one embodiment, it is provided a non-aqueous nanoemulgel made by the method disclosed above.

The present inventors found that the presence of a cosolvent like propylene glycol in a concentration in the nanoemulgel above 20% is important in contributing to the formation of nanoemulgel.

DESCRIPTION

Brief Description of the Drawings

FIG. 1 shows the effect of type of penetration enhancers on diffusion of LZ from NEGMS using Start™ membrane for 15 days. In FIG. 1, LZ=letrozole, NEGMS=Nano Emul Gel Matrix System, GMO=Glyceryl monooleate grade above 40% glycerylmonooleate content, PGL=Propylene Glycol Laurate, PGMC=Propylene Glycol Mono Caprylate, and Captex=Captex 170 EP (Caprylic/Capric Acid Ester of Saturated Fatty Alcohol C12-C18).

DETAILED DESCRIPTION

It is understood that, with regard to this description and the appended claims, any reference to any aspect of this invention made in the singular includes the plural and vice versa unless it is expressly stated or unambiguously clear from the context that such is not intended.

As used herein, any term of approximation such as, without limitation, "near," "about," "approximately," "substantially," "essentially," and the like, mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the word or phrase unmodified by the term of approximation. In general, but with the preceding discussion in mind, a numerical value herein that is modified by a word of approximation may vary from the stated value by up to ±10%, unless expressly stated otherwise.

As used herein, all technical terminology is intended to have the meaning that would be afforded such terminology by those skilled in the relevant art unless it is expressly stated or obvious from the language or context that a different meaning is intended.

As used herein, the term "emulgel" refers to an emulsion that has the characteristics of a gel, for example, having certain viscosity. Alternatively the term refers to a gel that has the characteristics of an emulsion, for example, being a mixture of two or more liquids that are normally immiscible where one liquid is dispersed as globules (dispersed phase) in the other liquid (continuous phase).

As used herein, the term "cosolvents" refers to solvents which are used together to dissolve a solute. As used herein, the term "solvent" can be one chemical compound or a mixture of two or more chemical compounds.

As used herein, the term "nanoglobule" refers to the droplet dispersed in the continuous phase having a diameter less than 500 nm.

As used herein, the term "emulsifying gelling agent" refers to a substance or a blend of substances that stabilizes and thickens an emulsion. The emulsifying gelling agent may be polymers and/or gel-forming surfactants that prevent the coalescence of droplets of the dispersed phase and increase the viscosity of the continuous phase.

As used herein, the term "penetration enhancer" refers to a chemical compound that enhances skin permeation of a therapeutic agent.

As used herein, the term "therapeutic agent" is used interchangeable with the term "drug" and refers to a chemical or biological substance intended for use in the cure, mitigation, treatment, or prevention of a disease.

As used herein, the term "pharmaceutical composition," the term "composition," and the term "non-aqueous nanoemulgel" may be used interchangeably.

As used herein, the term "penetrate" and the term "permeate" may be used interchangeably. The term "penetration" and the term "permeation" may be used interchangeably.

In one embodiment of the present invention, it is provided a non-aqueous nanoemulgel comprising a therapeutic agent, a hydrophilic continuous phase formed of cosolvents, an oily dispersed phase formed of an oil component, and an emulsifying gelling agent. The oil component comprises glycerylmonooleate (GMO) and isohexadecane, wherein the grade of GMO is that having more than 40% of glyceryl monooleate. In some embodiments, the oily dispersed phase forms nanoglobules. In some embodiments, the cosolvents form nanoglobules of the oily dispersed phase. The size of the nanoglobules is less than 500 nm in diameter. The nanoemulgel is a clear gel. In some embodiments, the content is by weight. In some embodiments, the content is by volume.

In some embodiments including any one of the foregoing embodiments, the concentration of the therapeutic agent in the nanoemulgel ranges from about 0.5% to about 10% w/w or w/v. In some embodiments, the therapeutic concentration is about 0.5%, about 1.0%, about 1.5%, about 2.0%, about 2.5%, about 3.0%, about 3.5%, about 4.0%, about 4.5%, about 4.5%, about 5.0%, about 5.5%, about 6.0%, about 6.5%, about 7.0%, about 7.5%, about 8.0%, about 8.5%, about 9.0%, about 9.5%, or about 10% w/w or w/v.

In some embodiments including any one of the foregoing embodiments, the GMO grade in the oil component or the oily phase has glyceryl monooleate content ranging from about 45% to about 95%, about 45% to about 90%, about 45% to about 85%, about 45% to about 80%, about 45% to about 75%, about 45% to about 70%, about 45% to about 65%, or about 45% to about 60%. In some embodiments, the GMO grade has glyceryl monooleate content ranging from about 50% to about 90%, or about 60% to about 90%, or about 70% to about 90%. In some embodiments, the GMO grade has glyceryl monooleate content about 50%, about 55%, about 60%, about 65%, about 70%, about 75%, about 80%, about 85%, about 90%, or about 95%. In some embodiments, the content is by weight. In some embodiments, the content is by volume.

In some embodiments including any one of the foregoing embodiments, the size of the nanoglobules ranges from about 10 nm to about 50 nm, from about 50 nm to about 400 nm, from about 50 nm to about 350 nm, from about 50 nm to about 200 nm, from about 50 nm to about 150 nm, or from about 50 nm to 100 nm, in diameter. In some embodiments, the size of the nanoglobules ranges from about 10 nm to about 50 nm, from about 100 nm to about 400 nm, from about 100 nm to about 350 nm, from about 100 nm to about 200 nm, or from about 100 nm to about 150 nm, in diameter. In some embodiments, the size of the nanoglobules is about 450 nm, about 400 nm, about 350 nm, about 300 nm, about 250 nm, about 200 nm, about 150 nm, about 100 nm, about 50 nm, about 40 nm, about 30 nm, about 20 nm, or about 10 nm in diameter.

In some embodiments including any one of the foregoing embodiments, the main factors which control the formation of the nanoemulgel comprising the therapeutic agent such as LZ are the grade of GMO which should have glyceryl monooleate content more than 40% and the presence of propylene glycol in an amount of 20% or more of the nanoemulgel. In some embodiments, the content is by weight. In some embodiments, the content is by volume.

In some embodiments including any one of the foregoing embodiments, the hydrophilic continuous phase comprises the cosolvents. In some embodiments, the oily dispersed phase comprises the oil component. In some embodiments including any one of the foregoing embodiments, the hydrophilic continuous phase consists of the cosolvents. In some embodiments, the oily dispersed phase consists of the oily component.

The nanoemugels provided herein have penetration power with emollient effects to the skin, and can be used as transdermal drug delivery systems. They can be applied to skin in a single dose that produces a pharmacologically effective blood concentration of the drug for immediate action if applied directly as a topical gel, or one week if used as a transdermal matrix patch containing doses equivalent to one-week administration, or up to one month if used as a transdermal matrix patch containing doses equivalent to one-month administration.

Skin penetration of the drug can be enhanced by using the basic formula of the nonaqueous nanoemulgel. The basic formula means that the nanoemulgels contain no skin penetration enhancer specifically described herein. In case the cosolvents, the surfactant, or the oil component have skin penetration enhancing effect, the basic formula contains no penetration enhancer other than the cosolvents, the surfactant, or the oil component. Further and significant penetration enhancing effect can be achieved by adding a skin penetration enhancer to the composition.

In some embodiments including any one of the foregoing embodiments, the nanoemulgel further comprises a penetration enhancer. In some embodiments, the penetration enhancer is selected from the group consisting of propylene glycol laurate, propylene glycol monocaprylate, and caprylic/capric acid ester of saturated C12-C18 fatty alcohol. Exemplary saturated C12-C18 fatty alcohols are lauryl alcohol (docecanol or 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), heptadecyl alcohol (1-n-heptadecanol, heptadecanol), stearyl alcohol (1-octadecanol), nonadecyl alcohol (1-nonadecanol) and arachidyl alcohol (1-eicosanol).

In some embodiments including any one of the foregoing embodiments, the therapeutic agent is a potent drug like an aromatase inhibitor. In some embodiments, the aromatase inhibitor is letrozole (trade name Femara) or anastrozole (Arimidex). Other aromatases inhibitors include exemestane (Aromasin), vorozole (Rivizor), formestane (Lentaron), and fadrozole (Afema).

In some embodiments including any one of the foregoing embodiments, the therapeutic agent is a NSAID. Exemplary NSAIDs are aspirin, celecoxib (trade name Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), and indomethacin (Indocin).

In some embodiments including any one of the foregoing embodiments, the cosolvents comprise propylene glycol and diethylene glycol ethyl ether (Transcutol). In some embodiments, one solvent of the cosolvents comprises propylene glycol and the other solvent comprises diethylene glycol ethyl ether (Transcutol). In some embodiments, one solvent of the cosolvents consists of propylene glycol and the other solvent consists of diethylene glycol ethyl ether (Transcutol). Transcutol is also known as diethylene glycol ethyl ether. Additional exemplary solvents that can be used with propylene glycol or can substitute for diethylene glycol ethyl ether (Transcutol) are glycerol, polyethylene glycol, ethanol, isopropanol, glycofurol, ethyl acetate, ethyl lactate, and pyrrolidones.

In some embodiments including any one of the foregoing embodiments, the oil component comprises GMO and isohexadecane. In some embodiments, the oil component comprises isohexadecane, isopropylmyristate, mineral oil, and GMO. In some embodiments, the oil component consists of GMO and isohexadecane.

In some embodiments including any one of the foregoing embodiments, the emulsifying gelling agent is a mixture of acrylamide/sodium acryloyldimethyl taurate copolymer, isohexadecane, and polyoxyethylene (20) sorbitan monooleate. SEPINEO P 600 contains isohexadecane, polysorbate 80, and acrylamide/sodium acrylolyldimethyl taurate copolymer. It can be used as the emulsifying gelling agent. The emulsifying gelling agent is a hydro-swelling droplet polymer and is able to thicken the hydrophilic phase while stabilize the oily dispersed phase.

In some embodiments including any one of the foregoing embodiments, the content of the hydrophilic phase or the cosolvents in the nanoemulgel ranges from about 50% to about 70% by weight or by volume. In some embodiments, the content of the hydrophilic phase or the cosolvents is about 50%, about 55%, about 60%, about 65%, or about 70% by weight or by volume. In some embodiments, the ratio of the cosolvents ranges from about 2:1 to 1:2. In some embodiments, the cosolvents comprise or consist of propylene glycol and diethylene glycol ethyl ether (Transcutol), and the content of propylene glycol is above 20% by weight or by volume. In some embodiments, the content of propylene glycol is about 25%, 30%, 35%, or 40% by weight or by volume.

In some embodiments including any one of the foregoing embodiments, the content of the oily dispersed phase or the oil component in the nanoemulgel ranges from about 10% to about 20% by weight or by volume. In some embodiments, the content of the oily dispersed phase or the oil component is about 10%, 15%, or 20% by weight or by volume.

In some embodiments including any one of the foregoing embodiments, the content of the emulsifying gelling agent in the nanoemulgel ranges from about 10% to about 20% by weight or by volume. In some embodiments, the content of the oily dispersed phase or the oil component is about 10%, 15%, or 20% by weight or by volume.

In one embodiment of the present invention, it is provided a method of making a non-aqueous nanoemulgel disclosed above, the method comprising:

mixing an oil component and an emulsifying gelling agent to form a first mixture; wherein the oil component comprises glyceryl monooleate (GMO) and isohexadecane; the grade of GMO is that having more than 40% glyceryl monooleate content; and preferably the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel. Each mixture is mixed well using appropriate mixing techniques known in the art. As an alternative, the therapeutic agent can be dissolved in the first cosolvent mixed with a portion of the second cosolvent to form a second mixture. In such case, the remaining portion of the second cosolvent is added to the third mixture thereby forming a nanoemulgel.

The formation of the nanoemulgel is spontaneous upon adding the second mixture to the first mixture, or adding a second cosolvent to the third mixture, or adding the remaining portion of the second cosolvent to the third mixture. The nanoemulgel is a clear gel.

In some embodiments, the first cosolvent comprises diethylene glycol ethyl ether (Transcutol) and the second cosolvent comprises propylene glycol. In some embodiments, the first cosolvent consists of diethylene glycol ethyl ether (Transcutol) and the second cosolvent consists of propylene glycol.

In some embodiments including any one of the foregoing embodiments, the method further comprises adding a penetration enhancer to the first mixture, the second mixture, the third mixture, or the final mixture.

In one embodiment of the present invention, it is provided a method of making a non-aqueous nanoemulgel, the method comprising:

mixing an oil component and an emulsifying gelling agent to form a first mixture; wherein the oil component comprises glycerylmonooleate (GMO) and isohexadecane; the grade of GMO is that having more than 40% glyceryl monooleate content; and preferably the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel. Each mixture is mixed well using appropriate mixing techniques known in the art. As an alternative, the therapeutic agent can be dissolved in the first cosolvent mixed with a portion of the second cosolvent to form a second mixture. In such case, the remaining portion of the second cosolvent is added to the third mixture thereby forming a nanoemulgel.

The formation of the nanoemulgel is spontaneous upon adding the second mixture to the first mixture, or adding the second cosolvent to the third mixture, or adding the remaining portion of the second cosolvent to the third mixture. The nanoemulgel is a clear gel.

In some embodiments including any one of the foregoing embodiments, the oil component forms an oily dispersed phase. In some embodiments, the cosolvents form a hydrophilic continuous phase. In some embodiments, the oily dispersed phase forms nanoglobules. In some embodiments, the cosolvents form nanoglobules of the oily dispersed phase. The size of the nanoglobules is less than 500 nm in diameter.

In some embodiments including any one of the foregoing embodiments, the first cosolvent comprises diethylene glycol ethyl ether (Transcutol) and the second cosolvent comprises propylene glycol. In some embodiments, the first cosolvent consists of diethylene glycol ethyl ether (Transcutol) and the second cosolvent consists of propylene glycol.

In some embodiments including any one of the foregoing embodiments, the concentration of the therapeutic agent in the nanoemulgel ranges from about 0.5% to about 10% w/w or w/v. In some embodiments, the therapeutic concentration is about 0.5%, about 1.0%, about 1.5%, about 2.0%, about 2.5%, about 3.0%, about 3.5%, about 4.0%, about 4.5%, about 4.5%, about 5.0%, about 5.5%, about 6.0%, about 6.5%, about 7.0%, about 7.5%, about 8.0%, about 8.5%, about 9.0%, about 9.5%, or about 10% w/w or w/v.

In some embodiments including any one of the foregoing embodiments, the GMO grade in the oil component or the oily phase has glyceryl monooleate content ranging from about 45% to about 95%, about 45% to about 90%, about 45% to about 85%, about 45% to about 80%, about 45% to about 75%, about 45% to about 70%, about 45% to about 65%, or about 45% to about 60%. In some embodiments, the GMO grade has glyceryl monooleate content ranging from about 50% to about 90%, or about 60% to about 90%, or about 70% to about 90%. In some embodiments, the GMO grade has glyceryl monooleate content about 50%, about 55%, about 60%, about 65%, about 70%, about 75%, about 80%, about 85%, about 90%, or about 95%. In some embodiments, the content is by weight. In some embodiments, the content is by volume.

In some embodiments including any one of the foregoing embodiments, the size of the nanoglobules ranges from about 10 nm to about 50 nm, from about 50 nm to about 400 nm, from about 50 nm to about 350 nm, from about 50 nm to 200 nm, from about 50 nm to about 150 nm, or from about 50 nm to 100 nm, in diameter. In some embodiments, the size of the nanoglobules ranges from about 10 nm to about 50 nm, from about 100 nm to about 400 nm, from about 100 nm to about 350 nm, from about 100 nm to 200 nm, or from about 100 nm to 150 nm, in diameter. In some embodiments, the size of the nanoglobules is about 450 nm, about 400 nm, about 350 nm, about 300 nm, about 250 nm, about 200 nm, about 150 nm, about 100 nm, about 50 nm, about 40 nm, about 30 nm, about 20 nm, or about 10 nm in diameter.

In some embodiments including any one of the foregoing embodiments, the main factors which control the formation of the nanoemulgel comprising a therapeutic agent such as LZ are the grade of GMO which should have glyceryl monooleate content more than 40% and the presence of propylene glycol in an amount of 20% or more of the nanoemulgel. In some embodiments, the content is by weight. In some embodiments, the content is by volume.

In some embodiments including any one of the foregoing embodiments, the above method further comprises adding a penetration enhancer to the first mixture or the second mixture. The penetration modifier is selected from the group consisting of propylene glycol laurate, propylene glycol monocaprylate, and caprylic/capric acid ester of saturated C12-C18 fatty alcohol. Exemplary saturated C12-C18 fatty alcohols are lauryl alcohol (docecanol or 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), heptadecyl alcohol (1-n-heptadecanol, heptadecanol), stearyl alcohol (1-octadecanol), nonadecyl alcohol (1-nonadecanol) and arachidyl alcohol (1-eicosanol).

In some embodiments, the therapeutic agent is a potent drug like an aromatase inhibitor. In some embodiments, the aromatase inhibitor is letrozole (trade name Femara) or anastrozole (Arimidex). Other aromatases inhibitors include exemestane (Aromasin), vorozole (Rivizor), formestane (Lentaron), and fadrozole (Afema). In some embodiments, the therapeutic agent is a NSAID. Exemplary NSAIDs are aspirin, celecoxib (trade name Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), and indomethacin (Indocin).

In some embodiments including any of the foregoing embodiments, one solvent of cosolvents comprises propylene glycol and the other solvent comprises diethylene glycol ethyl ether (Transcutol). In some embodiments, one solvent consists of propylene glycol and the other solvent consists of diethylene glycol ethyl ether (Transcutol). Transcutol is also known as diethylene glycol ethyl ether. Additional exemplary solvents that can be used with propylene glycol or can substitute for diethylene glycol ethyl ether (Transcutol) are glycerol, polyethylene glycol, ethanol, isopropanol, glycofurol, ethyl acetate, ethyl lactate, and pyrrolidones.

In one embodiment, it is provided a non-aqueous nanoemulgel made by the any of the methods disclosed above.

In accordance to the present invention, it is provided transdermal nanoemugels for systemic delivery of potent drugs like aromatase inhibitors letrozole and anastrozole. The transdermal nanoemugels can also be used for transdermal delivery of analgesic drugs such as nonsteroidal anti-inflammatory drugs (NSAIDs). The nanoemugels may include emulsifying gelling agents, surfactants, cosolvents, and oil components. Exemplary nonionic surfactants are polysorbates (Tween™), polyethoxylated alcohols, polyoxyethylene sorbitan, octoxynol (Triton X100™), Brij™ Surfactants, polyoxyl castor oil (Cremophor™) nonylphenol ethoxylate (Tergitol™), and poly(ethylene glycol)-block-poly(propylene glycol)-block-poly(ethylene glycol) (Ploxamer™) surfactants.

The transdermal nanoemugel compositions provided herein have penetration power with emollient effects to the skin. The transdermal nanoemugels can be used as transdermal drug delivery systems and contain a pharmaceutically or therapeutically effective amount of a drug. They can be applied to skin in a single dose that produces a pharmacologically effective blood concentration of the drug for immediate action if applied directly as topical gel, or one week if used as a transdermal matrix patch containing doses equivalent to one week administration or up to one month if used as a transdermal matrix patch containing doses equivalent to one month administration. The cosolvents form the hydrophilic continuous phase of the emulsion and dissolve the drug, e.g., letrozole. Exemplary cosolvents are propylene glycol and diethylene glycol ethyl ether (Transcutol).

The oily phase is formed of an oil component. Exemplary oil component is isohexadecane and glycerylmonooleate (GMO). The grade of glycerylmonooleate plays an important role in obtaining nanoemulgel. The present inventors surprisingly found that the GMO grade should be containing more than 40% as glyceryl monooleate. The higher the glycerylmonooleate content in the oily GMO component is the higher viscosity obtained for the nonaqueous nanoemulgel. It was found that 40% glyceryl monooleate content of GMO did not produce nanoemulgel and the gel was turbid and was less viscous, then by using anothergrade with 60% glycerl monooleate content with the same amount in the formula, the gel showed unexpectedly higher viscosity and nanoemulgel as indicated by clear gel. Exemplary emulsifying gelling agent is SEPINEO P 600 which contains isohexadecane, polysorbate 80 and acrylamide/sodium acryloyldimethyl taurate copolymer.

The nanoemulgels are clear gel. The droplets or globules of the compositions are less than 500 nm in diameter.

Skin penetration of the drug can be evaluated by diffusion of the drug through semisynthetic membranes. Diffusion of the drug through semisynthetic membranes was enhanced by using the basic formula of the nonaqueous nanoemulgel. The basic formula means that the nanoemulgels contain no skin penetration enhancer described herein. In case the cosovlents, the surfactant, or the oil component have skin penetration enhancing effect, the basic formula contains no penetration enhancer other than the cosolvents, the surfactant, or the oil component.

Significant penetration enhancing effect has been achieved by adding a skin penetration enhancer. Exemplary skin penetration enhancers are propylenglycol laurate, propyleneglycolmonocaprylate, and caprylic/capric acid ester of saturated C12-C18 fatty alcohol or similar components. Maximum penetration enhancing effect appears with nanoemulgels containing a skin penetration enhancer.

Depending on the nanoemulgels, the drug release may continue for at least one week, and up to one month. The present invention could be used as a transdermal matrix system for transdermal drug delivery system for potent drugs which could be applied as long as one month depending on the daily dose of the potent drug. For large dose drugs like NSAID, the present invention is suitable for direct topical application.

In accordance to the present invention, it is also provided a process of preparing the nanoemulgels. The process is simple and rapid, and the formation of the nanoemulgels are spontaneous.

The process can be a simple mixing process involving direct addition of components with minimum required mechanical stirring to form non-aqueous nanogemulgel which is characterized by being a clear gel.

The present inventors surprisingly found that the clear nanoemulgel is formed spontaneously with simple mixing by adding propylene glycol to the mixture containing all other components. The size of the nanoglobules is less than 500 nm. It was surprisingly found that the mixture composed of oily component, emulsifying gel, and transcutol solution of the drug and before adding propylene glycol was turbid non viscous. Once propylene glycol was added in certain amount it was suddenly changed to clear and viscous gel. The present invention differs from existing technologies and practices in that it is non-aqueous and it has simple and rapid preparation process. The non-aqueous nanoemulgels are formed spontaneously and stable which do not need to incorporate any physical stabilizer.

EXAMPLES

Example 1

Four samples of emulgels were prepared according to the formula in Table 1 below and the experiments described below.

TABLE 1

| Formula # | LZ | Mixture (GMO/SG) | PGMC | Captex | PGL | TC | PG | Gel Appearance |
|---|---|---|---|---|---|---|---|---|
| LZ/Basic Formula | 1.38 | 32.17 (14.3/17.87) | — | — | — | 39.53 | 26.92 | Clear Gel |
| LZ/PGL | 1.154 | 29.746 | — | — | 5.721 | 30.899 | 32.48 | Clear Gel |
| LZ/PGMC | 1.579 | 28.214 | 5.057 | — | — | 38.554 | 26.596 | Clear Gel |
| LZ/Captex | 1.50 | 32 | — | 5.0 | — | 35.0 | 26.0 | Clear Gel |

* LZ: Letrozole
* SG: Sepineo P600 (Seppic - France)
* GMO: Glyceryl monooleate, Grade having GMO content more than 40%.
* TC: Transcutol
* PG: Propylene Glycol.
* PGL: Propylene glycol laurate
* Captex: Captex 170 EP (Caprylic/Capric Acid Ester of Saturated Fatty Alcohol C12-C18).
* PGMC: Propylene Glycol Mono Caprylate.

A LZ basic emulgel was prepared using GMO as the oil component, SG as the emulsifying gelling agent, TC and PG as cosolvents. The basic LZ gel was clear.

Three additional LZ emulgels were prepared using PGL, Captex, and PGMC respectively as the penetration enhancer/modifier, in addition to the components in the basic formula. All three gels were clear.

It was also found that in case of LZ/Basic Formula if the type or grade of GMO is 40% glyceryl monooleate content the resultant emulgel is turbid and no more nanoemulgel, the globule size is more than 1000 nm.

Experiments:

Preparation of Gel Formulations

Sepineo 600 (SP) was mixed with glyceryl monooleate (GMO) on a heating water bath at 70° C. until a clear mixture was obtained (MIX 01). Letrozole (LZ) was dissolved in transcutol (TC) on a heating water bath at 70° C. until a clear solution was obtained (MIX 02). MIX 02 was added gradually to MIX 01 while both were hot and mixed well to afford a mixture (MIX 03).

To form the final gel, propylene glycol was added gradually to MIX 03 with good mixing after each addition. A nanoemulgel was characterized by forming a transparent clear gel. In case of formulations containing penetration enhancer, the required amount was added to MIX 02 and mixed well and then added to MIX 01 to form MIX 03. To form the final gel propylene glycol was added gradually to MIX 03 with good mixing after each addition. The clear gel was still maintained.

Alternative method: half the amount of propylene glycol (PG) was added to LZ solution in transcutol (MIX 02). MIX 02 was added gradually to MIX 01 while both were hot and mixed well (MIX 03). To form the final gel the other half of PG was added gradually to MIX 03 with good mixing after each addition. A nanoemulgel was characterized by forming a transparent clear gel. In case of formulations containing penetration enhancer, the required amount was added to MIX 02 and mixed well and then added to MIX 01 to form MIX 03. The clear gel was still maintained.

What is claimed is:

1. A non-aqueous nanoemulgel comprising:

a therapeutic agent, a hydrophilic continuous phase formed of cosolvents, an oily dispersed phase formed of an oil component, wherein the oily component comprises glyceryl monooleate (GMO) and isohexadecane, and an emulsifying gelling agent, wherein the type or grade of GMO is that containing more than 40% glycerl monooleate, the cosolvents comprise propylene glycol and diethylene glycol ethyl ether, the cosolvents form nanoglobules of the oily dispersed phase, the size of the nanoglobules is less than 500 nm in diameter, and the nanoemulgel is a clear gel.

2. The nanoemulgel of claim 1, further comprising a penetration enhancer.

3. The nanoemulgel of claim 1 or 2, wherein the therapeutic agent is a potent drug.

4. The nanoemulgel of any of claims 1 to 3, wherein the therapeutic agent is an aromatase inhibitor.

5. The nanoemulgel of claim 4, wherein the aromatase inhibitor is letrozole or anastrozole.

6. The nanoemulgel of claim 1 or 2, wherein the therapeutic agent is a NSAID.

7. The nanoemulgel of any of claims 1-6, wherein the cosolvents consist of propylene glycol and diethylene glycol ethyl ether.

8. The nanoemulgel of any of claims 1-7, wherein the oil component consists of GMO and isohexadecane.

9. The nano-emulgel of any of claims 1-8, wherein the emulsifying gelling agent is a mixture of acrylamide/sodium acryloyldimethyl taurate copolymer, isohexadecane, and polyoxyethylene (20) sorbitan monooleate.

10. The nanoemulgel of any of claims 1-8, wherein the grade of GMO is that containing about 50%, about 55%, about 60%, about 65%, about 70%, about 75%, about 80%, about 85%, about 90%, or about 95% of glyceryl monooleate.

11. The nanoemulgel of any of claims 2-10, wherein the penetration modifier is selected from the group consisting of propylene glycol laurate, propylene glycol monocaprylate, and caprylic/capric acid ester of a saturated C12-C18 fatty alcohol.

12. A method of making the non-aqueous nanoemulgel of any one of claims 1-11, the method comprising:

mixing an oil component and an emulsifying gelling agent to form a first mixture;

wherein the oil component comprises glycerylmonooleate (GMO) and isohexadecane; the grade of GMO is that having more than 40% glyceryl monooleate content; and the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel;

wherein each mixture is mixed well; and the first cosolvent comprises diethylene glycol ethyl ether and the second cosolvent comprises propylene glycol.

13. The method of claim 12, further comprising:

adding a penetration enhancer to the first mixture, the second mixture, the third mixture, or the final mixture.

14. The method of claim 12 or 13, wherein the therapeutic agent is a potent drug or an aromatase inhibitor.

15. The method of claim 14, wherein the aromatase inhibitor is letrozole or anastrozole.

16. The method of claim 12, wherein the therapeutic agent is a NSAID.

17. The method of any of claims 12-16, wherein the oil component consists of GMO and isohexadecane.

18. The method of any of claims 12-17, wherein the first solvent consists of diethylene glycol ethyl ether and the second solvent consists of propylene glycol.

19. The method of any of claims 12-18, wherein the emulsifying gelling agent is a mixture of acrylamide/sodium acryloyldimethyl taurate copolymer, isohexadecane, and polyoxyethylene (20) sorbitan monooleate.

20. The method of any of claims 12-19, wherein the grade of GMO is that containing about 50%, about 55%, about 60%, about 65%, about 70%, about 75%, about 80%, about 85%, about 90%, or about 95% of glyceryl monooleate.

21. The method of any of claims 13-20, wherein the penetration enhancer is selected from the group consisting of propylene glycol laurate, propylene glycol monocaprylate, and caprylic/capric acid ester of saturated C12-C18 fatty alcohol.

22. A method of making a non-aqueous nanoemulgel, the method comprising:

mixing an oil component and an emulsifying gelling agent to form a first mixture;

wherein the oil component comprises glycerylmonooleate (GMO) and isohexadecane; the grade of GMO is that having more than 40% glyceryl monooleate content; and the emulsifying gelling agent is SEPINEO P 600;

dissolving a therapeutic agent in a first cosolvent to form a second mixture;

adding the second mixture to the first mixture to form a third mixture; and adding a second cosolvent to the third mixture thereby forming a non-aqueous nanoemulgel;

wherein each mixture is mixed well;

the first cosolvent comprises diethylene glycol ethyl ether and the second cosolvent comprises propylene glycol; and the nanoemulgel is a clear gel.

23. The method of claim 22, further comprising adding a penetration enhancer to the first mixture, the second mixture, the third mixture, or the final mixture.

24. The method of claim 22 or 23, wherein the therapeutic agent is a potent drug or an aromatase inhibitor.

25. The method of claim 24, wherein the aromatase inhibitor is letrozole or anastrozole.

26. The method of claim 22 or 23, wherein the therapeutic agent is a NSAID.

27. The method of any claims 22-26, wherein the oil component consists of GMO and isohexadecane.

28. The method of any of claims 22-27, wherein the first cosolvent consists of diethylene glycol ethyl ether and the second cosolvent consists of propylene glycol.

29. The method of any of claims 22-28, wherein the emulsifying gelling agent is a mixture of acrylamide/sodium acryloyldimethyl taurate copolymer, isohexadecane, and polyoxyethylene (20) sorbitan monooleate.

30. The method of any of claims 22-29, wherein the grade of GMO is that containing about 50%, about 55%, about 60%, about 65%, about 70%, about 75%, about 80%, about 85%, about 90%, or about 95% of glyceryl monooleate.

31. The method of any of claims 23-30, wherein the penetration modifier is selected from the group consisting of propylene glycol laurate, propylene glycol monocaprylate, and caprylic/capric acid ester of saturated C12-C18 fatty alcohol.

32. A non-aqueous nanoemulgel, made by the method of any of claims 22-31.

* * * * *